US009539430B2

(12) United States Patent
Mishra et al.

(10) Patent No.: US 9,539,430 B2
(45) Date of Patent: Jan. 10, 2017

(54) DYNAMIC COMPLIANCE VOLTAGE MANAGEMENT FOR AN IMPLANTABLE STIMULATOR

(75) Inventors: Lakshmi N. Mishra, Valencia, CA (US); Logan P. Palmer, Santa Monica, CA (US); Manohar Joshi, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 1667 days.

(21) Appl. No.: 12/648,611

(22) Filed: Dec. 29, 2009

(65) Prior Publication Data

US 2011/0160799 A1 Jun. 30, 2011

(51) Int. Cl.
*A61N 1/00* (2006.01)
*A61N 1/37* (2006.01)
*A61N 1/36* (2006.01)
*H02J 7/02* (2016.01)

(52) U.S. Cl.
CPC ........... *A61N 1/371* (2013.01); *A61N 1/36032* (2013.01); *H02J 7/025* (2013.01)

(58) Field of Classification Search
CPC ....... A61N 1/36032; A61N 1/371; H02J 7/025
USPC ......................................... 607/33, 55–57, 61
See application file for complete search history.

(56) References Cited

U.S. PATENT DOCUMENTS 5,549,658 A * 8/1996 Shannon ............ A61N 1/36032 607/56
5,876,425 A 3/1999 Gord et al.
6,289,246 B1 9/2001 Money
6,810,289 B1 10/2004 Shaquer
7,171,273 B2 1/2007 Shaquer
7,444,181 B2 10/2008 Shi et al.
2001/0031909 A1 10/2001 Faltys et al.
2004/0082985 A1* 4/2004 Faltys et al. .................. 607/116
2007/0135868 A1 6/2007 Shi et al.
2008/0015657 A1* 1/2008 Haefner .......................... 607/62

OTHER PUBLICATIONS

International Search Report and Written Opinion received in International Application No. PCT/US2010/062296, dated Oct. 7, 2011.

* cited by examiner

*Primary Examiner* — William Levicky
*Assistant Examiner* — Lindsey G Hankins
(74) *Attorney, Agent, or Firm* — ALG Intellectual Property, LLC

(57) ABSTRACT

An exemplary method includes generating, by an external control device selectively and communicatively coupled to an implantable stimulator, a calibration table indicating transmit power levels required to achieve a plurality of distinct combinations of compliance voltages and maximum stimulation current levels by the implantable stimulator, determining, by the external control device, a maximum stimulation current level to be delivered by the implantable stimulator via one or more electrodes to one or more stimulation sites within a patient during a stimulation frame, determining, by the external control device, an optimal compliance voltage that allows the implantable stimulator to deliver the determined maximum stimulation current level, and selecting, by the external control device in accordance with the calibration table, a transmit power level that results in the implantable stimulator operating at substantially the optimal compliance voltage during the stimulation frame. Corresponding methods, apparatuses and systems are also disclosed.

23 Claims, 11 Drawing Sheets

700

702
704

| Compliance Voltage (V) | Max. Stim. Current Level (μA) | Transmit Power Level Required (mW) |
|---|---|---|
| 8 | 1000 | 70 |
| 7 | 1000 | 65 |
| 6 | 1000 | 60 |
| 5 | 1000 | 55 |
| 4 | 1000 | 50 |
| 8 | 800 | 60 |
| 7 | 800 | 50 |
| . | . | . |
| . | . | . |
| 4 | 100 | 35 |

700

702

704

| Compliance Voltage (V) | Max. Stim. Current Level (µA) | Transmit Power Level Required (mW) |
|---|---|---|
| 8 | 1000 | 70 |
| 7 | 1000 | 65 |
| 6 | 1000 | 60 |
| 5 | 1000 | 55 |
| 4 | 1000 | 50 |
| 8 | 800 | 60 |
| 7 | 800 | 50 |
| . | . | . |
| . | . | . |
| 4 | 100 | 35 |

DYNAMIC COMPLIANCE VOLTAGE MANAGEMENT FOR AN IMPLANTABLE STIMULATOR

BACKGROUND

Compliance voltage in an implantable stimulator governs a maximum level of stimulation current that can be delivered by the implantable stimulator via one or more electrodes to one or more stimulation sites within a patient. A compliance voltage that is higher than absolutely necessary to generate and deliver a desired stimulation current causes the implantable stimulator to operate in an inefficient manner. For example, the excess compliance voltage contributes to power loss that results in a reduced battery life of the implantable stimulator. On the other hand, a compliance voltage less than that which is needed to generate and deliver a desired stimulation current inhibits optimal stimulation performance by the implantable stimulator. For example, a sub-optimal compliance voltage limits the maximum stimulation rate at which the implantable stimulator may apply stimulation current to the one or more stimulation sites, causes undesirable stimulation artifacts, and diminishes an overall experience of the patient with the implantable stimulator.

Hence, it is desirable to maintain a compliance voltage at which an implantable stimulator operates at an optimal level. Unfortunately, maximum stimulation current level requirements vary significantly from situation to situation and from patient to patient, thereby resulting in corresponding variations in the optimal compliance voltage for these patients. For example, maximum stimulation current level requirements for a cochlear implant patient may vary depending on the particular listening environment in which the patient is situated, changes in electrode impedance, and changes in relative positioning of a cochlear stimulator implanted in the patient and its corresponding externally located sound processor. Because of such variations in maximum stimulation current level requirements, maintaining a fixed compliance voltage that is high enough to always account for a worst-case scenario is wasteful.

SUMMARY

An exemplary method of compliance voltage management includes: (1) generating, by an external control device selectively and communicatively coupled to an implantable stimulator, a calibration table indicating transmit power levels required to achieve a plurality of distinct combinations of compliance voltages and maximum stimulation current levels by the implantable stimulator; (2) determining, by the external control device, a maximum stimulation current level to be delivered by the implantable stimulator via one or more electrodes to one or more stimulation sites within a patient during a stimulation frame; (3) determining, by the external control device, an optimal compliance voltage that allows the implantable stimulator to deliver the determined maximum stimulation current level; and (4) selecting, by the external control device in accordance with the calibration table, a transmit power level that results in the implantable stimulator operating at substantially the optimal compliance voltage during the stimulation frame.

An exemplary apparatus for use with an implantable stimulator system includes: (1) a communication facility configured to transmit a power signal to an implantable stimulator; (2) a calibration facility configured to generate a calibration table indicating transmit power levels required to achieve a plurality of distinct combinations of compliance voltages and maximum stimulation current levels by the implantable stimulator; and (3) a compliance voltage facility configured to (a) determine a maximum stimulation current level to be delivered by the implantable stimulator via one or more electrodes to one or more stimulation sites within a patient during a stimulation frame, (b) determine an optimal compliance voltage that allows the implantable stimulator to deliver the determined maximum stimulation current level, and (c) select, in accordance with the calibration table, a transmit power level that results in the implantable stimulator operating at substantially the optimal compliance voltage during the stimulation frame.

An exemplary cochlear implant system includes: (1) an implantable cochlear stimulator configured to generate and apply stimulation current to one or more stimulation sites within a cochlea of a patient via one or more electrodes, and (2) a sound processor selectively and communicatively coupled to the implantable cochlear stimulator. The sound processor is configured to: (a) transmit a power signal to the implantable cochlear stimulator, (b) generate a calibration table indicating transmit power levels required to achieve a plurality of distinct combinations of compliance voltages and maximum stimulation current levels by the implantable cochlear stimulator, (c) determine a maximum stimulation current level to be delivered by the implantable cochlear stimulator during a stimulation frame, (d) determine an optimal compliance voltage that allows the implantable cochlear stimulator to deliver the determined maximum stimulation current level, and (e) select, in accordance with the calibration table, a transmit power level that results in the implantable cochlear stimulator operating at substantially the optimal compliance voltage during the stimulation frame.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7 illustrates an exemplary calibration table according to principles described herein.

DETAILED DESCRIPTION

Methods, apparatuses, and systems for dynamically managing a compliance voltage for an implantable stimulator are described herein. In some examples, an external control device may be selectively and communicatively coupled to the implantable stimulator and configured to transmit a power signal to the implantable stimulator from which the implantable stimulator derives a compliance voltage. The external control device may be further configured to generate a calibration table indicating various transmit power levels required to achieve a plurality of distinct combinations of compliance voltages and maximum stimulation current levels by the implantable stimulator, determine a maximum stimulation current level to be delivered by the implantable stimulator via one or more electrodes to one or more stimulation sites within a patient during a stimulation frame, determine an optimal compliance voltage that allows the implantable stimulator to deliver the determined maximum stimulation current level, and use the calibration table to select a transmit power level that results in the implantable stimulator operating at substantially the optimal compliance voltage during the stimulation frame.

As will be described in more detail below, the methods, apparatuses, and systems described herein dynamically maintain a compliance voltage of an implantable stimulator at an optimal level by adjusting a transmit power level of a power signal supplied to the implantable stimulator. Advantageously, the compliance voltage may be dynamically maintained at an optimal level without any real-time feedback from the implantable stimulator while the stimulation is taking place. Rather, as will be described in more detail below, the compliance voltage is maintained in a feed-forward manner by selecting the transmit power level from a pre-populated calibration table. The calibration table may be periodically and automatically updated in order to account for any changes in electrode impedance, power transfer efficiency, and/or physiological characteristics (e.g., flap thickness, hair growth, etc.).

Moreover, the methods apparatuses, and systems described herein may optimize performance of the implantable stimulator. For example, by maintaining an optimal compliance voltage, battery life of the implantable stimulator may be extended and increased stimulation rates of the implantable stimulator may be achieved.

As used herein, a "stimulation frame" refers to any period of time in which electrical stimulation is applied to a patient by an implantable stimulator. For example, a stimulation frame may refer to a time period in which a predetermined number of stimulation pulses are delivered to one or more stimulation sites within a patient via one or more electrodes.

Figure 1:
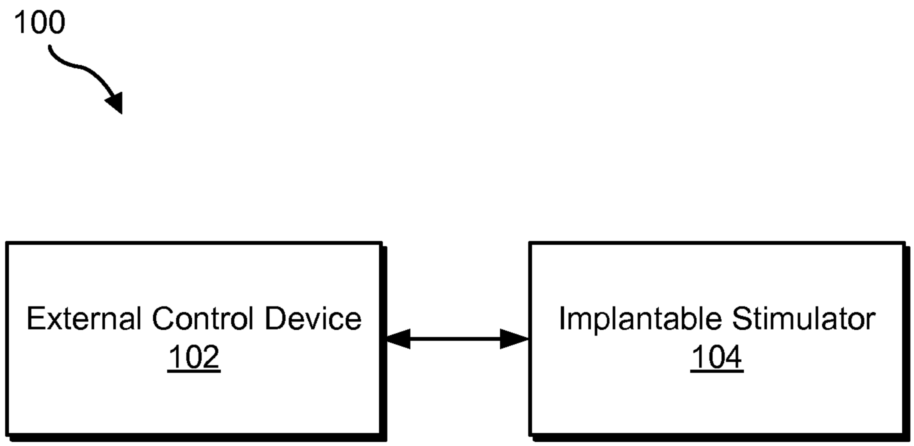
FIG. 1 illustrates an exemplary stimulation system according to principles described herein.

FIG. 1 illustrates an exemplary stimulation system 100. As shown in FIG. 1, stimulation system 100 may include an external control device 102 and an implantable stimulator 104 configured to communicate with one another.

Implantable stimulator 104 may be configured to generate and apply stimulation current (also referred to as "electrical current" and/or "stimulation pulses") to one or more stimulation sites within a patient in accordance with one or more stimulation parameters transmitted thereto by external control device 102. The stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

In addition to transmitting one or more stimulation parameters to implantable stimulator 104, external control device 102 may be configured to transmit a power signal to implantable stimulator 104. Implantable stimulator 104 may derive a compliance voltage from the transmitted power signal. The compliance voltage governs a maximum stimulation current level that implantable stimulator 104 may apply to one or more stimulation sites.

As will be described in more detail below, external control device 102 may be configured to dynamically adjust a transmit power level of the power signal in order to maintain an optimal compliance voltage within implantable stimulator 104 regardless of fluctuations in maximum stimulation current level requirements. As will also be described in more detail below, the dynamic adjustment of the transmit power level may be performed by external control device 102 without real-time feedback from implantable stimulator 104, thus obviating the processing and power requirements associated with real-time transmission of feedback data by implantable stimulator 104.

Stimulation system 100 may be implemented by any combination of devices configured to apply stimulation current to one or more stimulation sites within a patient. For example, stimulation system 100 may be implemented by a cochlear implant system having an implantable cochlear stimulator that is controlled by an externally worn speech processor, a spinal cord stimulation system, an implantable pulse generator, and/or any other stimulation device as may serve a particular application. An exemplary cochlear implant system will be described in more detail below.

Stimulation system 100, including external control device 102 and implantable stimulator 104, may include any hardware, computer-implemented instructions (e.g., software), firmware, or combinations thereof configured to perform one or more of the processes described herein. For example, stimulation system 100, including external control device 102 and implantable stimulator 104, may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within external control device 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other tangible medium from which a computing device can read.

Figure 2:
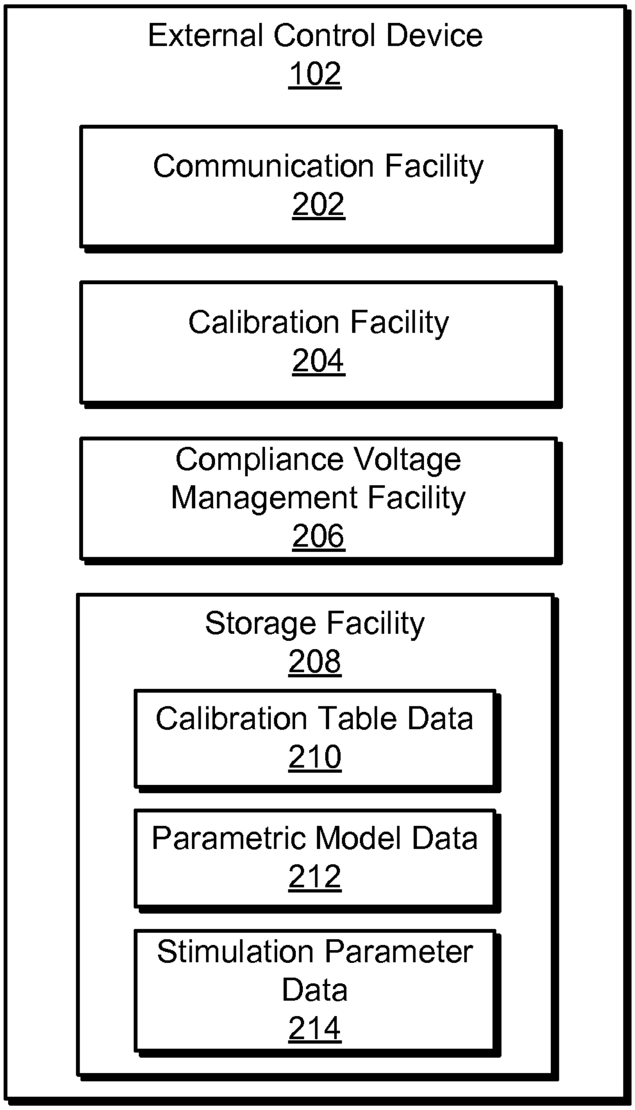
FIG. 2 illustrates exemplary components of an external control device according to principles described herein.

FIG. 2 illustrates exemplary components of external control device 102. As shown in FIG. 2, external control device 102 may include a communication facility 202, a calibration facility 204, a compliance voltage management facility 206, and a storage facility 208, which may be in communication with one another using any suitable communication technologies. Each of these facilities 202-208 may include or be implemented by any combination of hardware, software, and/or firmware as may serve a particular application. For example, one or more of facilities 202-208 may include or be implemented by a computing device or processor configured to perform one or more of the functions described herein. It will also be recognized that one or more of facilities 202-208 may be optionally not included within external control device 102. Facilities 202-208 will now be described in more detail.

Communication facility 202 may be configured to facilitate communication between external control device 102 and implantable stimulator 104. For example, communication facility 202 may include one or more coils configured to wirelessly transmit a control signal representative of one or more stimulation parameters to implantable stimulator 104. Communication facility 202 may be additionally or alternatively configured to transmit a power signal to implantable stimulator 104 by way of the one or more coils. As will be described in more detail below, implantable stimulator 104 may derive a compliance voltage from the transmitted power signal.

Calibration facility 204 may be configured to perform a calibration procedure that characterizes a power transfer efficiency of system 100. In other words, calibration facility 204 may perform a series of tests to determine various transmit power levels of the power signal transmitted by communication facility 202 that are required to achieve several different combinations of compliance voltages and maximum stimulation current levels in implantable stimulator 104. Calibration facility 204 may be further configured to record the results of the tests in the form of a calibration table. An exemplary calibration table and exemplary heuristics that may be used to generate the calibration table will be described in more detail below.

Calibration facility 204 may additionally or alternatively be configured to generate a parametric model that may be used to select a transmit power level that results in implantable stimulator 104 operating an optimal compliance voltage during a particular stimulation frame. An exemplary parametric model and exemplary heuristics that may be used to generate the parametric model will be described in more detail below.

In some examples, calibration facility 204 may perform the calibration process (i.e., generate a calibration table and/or a parametric model) each time external control device 102 is powered on or coupled to implantable stimulator 104. Additionally or alternatively, calibration facility 204 may perform the calibration process on a periodic basis, in response to one or more predefined events, and/or at any other time as may serve a particular application.

Compliance voltage management facility 206 may be configured to dynamically manage the compliance voltage at which implantable stimulator 104 operates. To this end, compliance voltage management facility 206 may be configured to determine a maximum stimulation current level to be delivered by implantable stimulator 104 via one or more electrodes to one or more stimulation sites within a patient during a stimulation frame, determine an optimal compliance voltage that allows implantable stimulator 104 to deliver stimulation current at the determined maximum stimulation current level, and use the calibration table and/or parametric model generated by calibration facility 204 to select a transmit power level that results in implantable stimulator 104 operating at substantially the optimal compliance voltage during the stimulation frame. This process may be repeated for each subsequent stimulation frame. In this manner, compliance voltage management facility 206 may maintain the compliance voltage of implantable stimulator 104 at an optimal level, regardless of changes in the maximum stimulation current level required from one stimulation frame to the next. In some examples, the optimal compliance voltage for a particular stimulation frame may be predicted in advance so that an appropriate transmit power level may be selected prior to an occurrence of the stimulation frame.

Compliance voltage management facility 206 may be further configured to direct implantable stimulator 104 to measure or otherwise monitor an impedance of one or more electrodes communicatively coupled to implantable stimulator 104. An electrode impedance may be dependent on any of a number of factors. For example, the impedance of an electrode may be dependent on one or more physiological properties of the tissue where the electrode is implanted, the composition of the electrode itself, and/or any other factor as may serve a particular application. As will be described in more detail below, electrode impedances associated with one or more electrodes may be utilized by compliance voltage management facility 206 to select a transmit power level that results in an optimal compliance voltage in implantable stimulator 104.

Storage facility 208 may be configured to maintain calibration table data 210 representative of the calibration table generated by calibration facility 204, parametric model data 212 representative of the parametric model generated by calibration facility 204, and/or stimulation parameter data 214 representative of one or more stimulation parameters configured to define the stimulation current generated by implantable stimulator 104. Storage facility 208 may be configured to maintain additional or alternative data as may serve a particular application.

Figure 3:
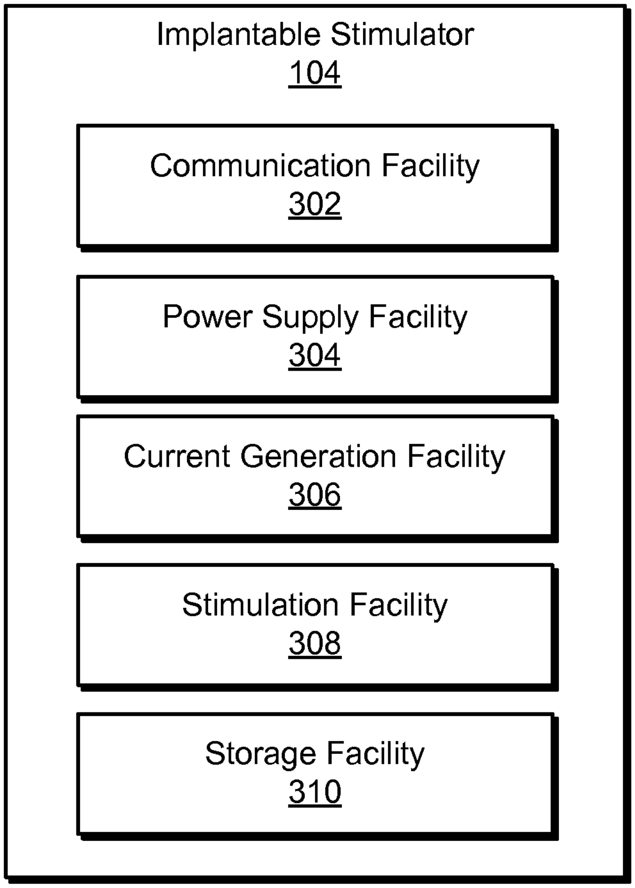
FIG. 3 illustrates exemplary components of an implantable stimulator according to principles described herein.

FIG. 3 illustrates exemplary components of implantable stimulator 104. As shown in FIG. 3, implantable stimulator 104 may include a communication facility 302, a power supply facility 304, a current generation facility 306, a stimulation facility 308, and a storage facility 310, which may be in communication with one another using any suitable communication technologies. Each of these facilities 302-310 may include any combination of hardware, software, and/or firmware as may serve a particular application. For example, one or more of facilities 302-310 may include a computing device or processor configured to perform one or more of the functions described herein. Facilities 302-310 will now be described in more detail.

Communication facility 302 may be configured to facilitate communication between implantable stimulator 104 and external control device 102. For example, communication facility 302 may include one or more coils configured to receive control signals and/or power signals from external control device 102. Communication facility 302 may additionally or alternatively be configured to transmit one or more status signals and/or other data to external control device 102.

Power supply facility 304 may be configured to provide power to various components included within implantable stimulator 104. To this end, power supply facility 304 may be configured to derive a compliance voltage from a power signal received from external control device 102. The compliance voltage may be used by current generation facility 304 to generate stimulation current and/or by any other component within implantable stimulator 104.

Figure 4:
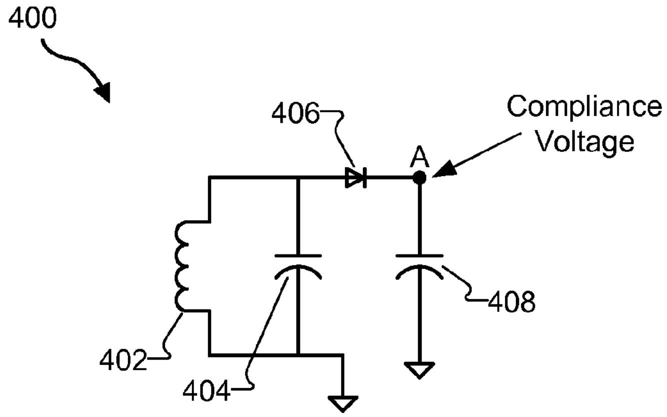
FIG. 4 illustrates an exemplary tank circuit according to principles described herein.

In some examples, communication facility 302 and power supply facility 304 may be implemented by a tank circuit. FIG. 4 illustrates an exemplary tank circuit 400 that may implement communication facility 302 and power supply facility 304. As shown in FIG. 4, tank circuit 400 may include a receiving coil 402 in parallel with a capacitor 404. Tank circuit 400 may further include a diode 406 and a capacitor 408 in series one with another, the combination thereof also being in parallel with capacitor 404. Receiving coil 402 is configured to receive a power signal transmitted by a corresponding transmit coil associated with external control device 102. A compliance voltage may be derived from the received power signal by passing the received signal through diode 406. As shown in FIG. 4, the compliance voltage may be equal to the voltage at node A. The compliance voltage may be generated from a received power signal in any other suitable manner as may serve a particular application.

Returning to FIG. 3, current generation facility 306 may be configured to generate stimulation current in accordance with one or more stimulation parameters received from external control device 102. To this end, current generation facility 306 may include one or more current generators and/or any other circuitry configured to facilitate generation of stimulation current. For example, current generation facility 306 may include an array of independent current generators each corresponding to a distinct electrode or channel. As discussed previously, a maximum stimulation current level that each current generator is capable of producing is dependent in part on the compliance voltage produced by power supply facility 304.

Stimulation facility 308 may be configured to facilitate application of the stimulation current generated by current generation facility 306 to one or more stimulation sites within the patient in accordance with one or more stimulation parameters received from external control device 102. To this end, as will be illustrated in more detail below, stimulation facility 308 may be configured to interface with one or more electrodes disposed on a lead that may be inserted within the patient (e.g., within the cochlea).

Storage facility 310 may be configured to maintain data generated and/or utilized by implantable stimulator 104. For example, storage facility 310 may maintain data representative of one or more stimulation parameters configured to define the stimulation current generated and applied by implantable stimulator 104.

Figure 5:
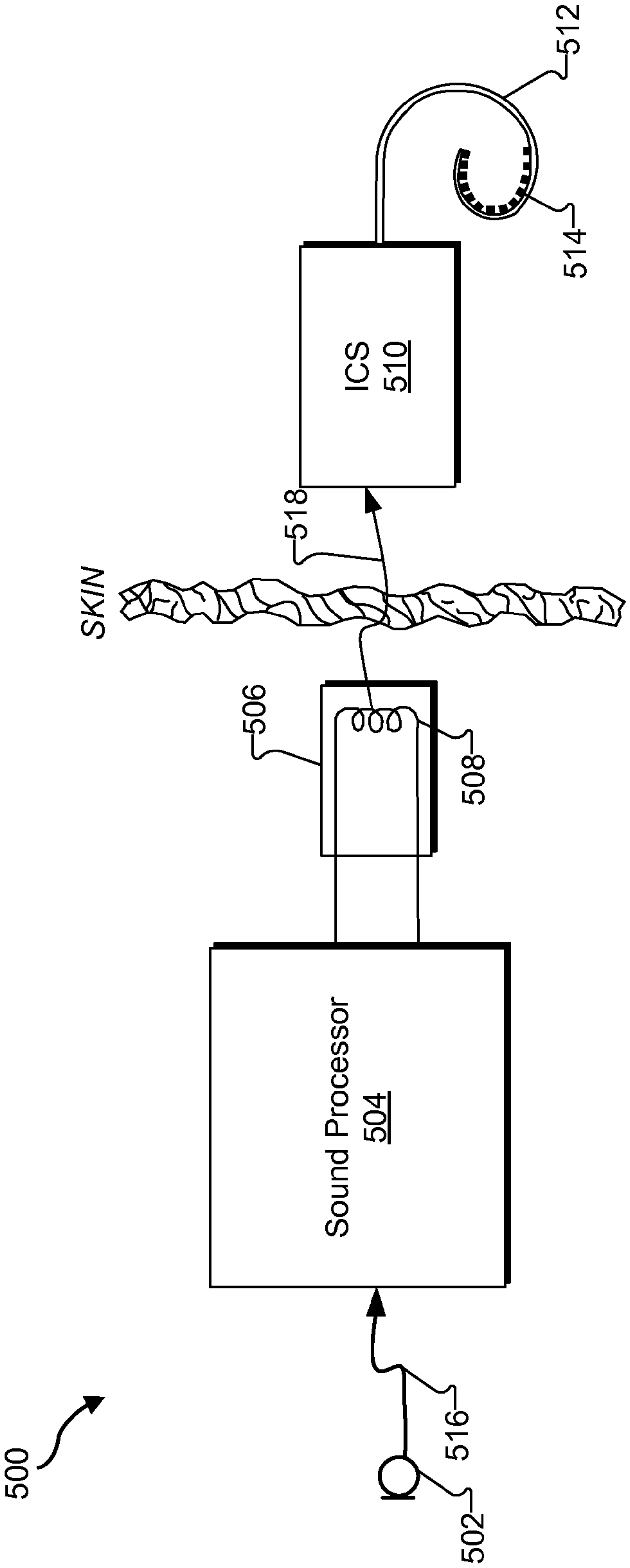
FIG. 5 illustrates an exemplary cochlear implant system according to principles described herein.

As mentioned, stimulation system 100 may be implemented by any combination of devices configured to apply stimulation current to one or more stimulation sites within a patient. For example, FIG. 5 illustrates an exemplary cochlear implant system 500 that may implement stimulation system 100. Cochlear implant system 500 may include a microphone 502, a sound processor 504, a headpiece 506 having a coil 508 disposed therein, an implantable cochlear stimulator ("ICS") 510, a lead 512, and a plurality of electrodes 514 disposed on the lead 512. Additional or alternative components may be included within cochlear implant system 500 as may serve a particular application. The facilities described herein may be implemented by or within one or more components shown within FIG. 5. For example, communication facility 212 may be implemented by headpiece 506 and coil 508. Calibration facility 204, compliance voltage management facility 206, and/or storage facility 208 may be implemented by sound processor 504. Communication facility 302, power supply facility 304, current generation facility 306, stimulation facility 308, and storage facility 310 may be implemented by implantable cochlear stimulator 508.

As shown in FIG. 5, microphone 502, sound processor 504, and headpiece 506 are located external to a cochlear implant patient. Microphone 502 may detect an audio signal and convert the detected signal to a corresponding electrical signal. The electrical signal may be sent from microphone 502 to sound processor 504 via a communication link 514, which may include a telemetry link, a wire, and/or any other suitable communication link.

Sound processor 504 is configured to process the converted audio signal in accordance with a selected sound processing strategy to generate appropriate stimulation parameters for controlling implantable cochlear stimulator 510. Sound processor 504 may include or be implemented within a behind-the-ear ("BTE") unit, a portable speech processor ("PSP"), and/or any other sound processing unit as may serve a particular application. Exemplary components of sound processor 504 will be described in more detail below.

Sound processor 504 may be configured to transcutaneously transmit data (e.g., data representative of one or more stimulation parameters) and power signals to implantable cochlear stimulator 504 via coil 508. As shown in FIG. 5, coil 508 may be housed within headpiece 506, which may be affixed to a patient's head and positioned such that coil 508 is communicatively coupled to a corresponding coil (e.g., receiving coil 402) included within implantable cochlear stimulator 510. In this manner, data and power signals may be wirelessly transmitted between sound processor 504 and implantable cochlear stimulator 510 via communication link 518. It will be understood that data communication link 118 may include a bi-directional communication link and/or one or more dedicated uni-directional communication links. In some alternative embodiments, sound processor 504 and implantable cochlear stimulator 510 may be directly connected with one or more wires or the like.

Implantable cochlear stimulator 510 may be configured to generate stimulation current representative of an audio signal detected by microphone 502 in accordance with one or more stimulation parameters transmitted thereto by external control device 102. Implantable cochlear stimulator 510 may be further configured to apply the stimulation current to one or more stimulation sites within the cochlea via one or more electrodes 514 disposed along lead 512.

To facilitate application of the stimulation current generated by implantable cochlear stimulator 510, lead 512 may be inserted within a duct of the cochlea such that electrodes 514 are in communication with one or more stimulation sites within the cochlea. As used herein, the term "in communication with" refers to electrodes 514 being adjacent to, in the general vicinity of, in close proximity to, directly next to, or directly on the stimulation site. Any number of electrodes 514 (e.g., sixteen) may be disposed on lead 512 as may serve a particular application.

Implantable cochlear stimulator 510 may be further configured to derive a compliance voltage from a power signal transmitted thereto by sound processor 504. To this end, implantable cochlear stimulator 510 may include any combination of circuitry and/or other components configured to process the power signal and derive the compliance voltage therefrom. For example, implantable cochlear stimulator

510 may include a tank circuit similar to tank circuit 400 described in connection with FIG. 4.

As mentioned, maximum stimulation current level requirements for implantable stimulator 104 may vary from stimulation frame to stimulation frame. Hence, the compliance voltage needed to achieve the varying levels of stimulation current also varies from stimulation frame to stimulation frame. For example, if the maximum stimulation current level to be delivered to a 10 kOhm load (i.e., tissue having an impedance of 10 kOhm) during a particular stimulation frame is 500 microamps, the required compliance voltage is 5 volts. During a subsequent stimulation frame, the maximum stimulation current level to be delivered to the 10 kOhm load may only be 100 microamps. The required compliance voltage to generate the 100 microamps is 1 volt. However, if the compliance voltage is fixed at 5 volts for both stimulation frames, a majority of the compliance voltage (i.e., 4 volts) is wasted during the stimulation frame that only requires 1 volt.

It is therefore desirable to dynamically adjust the compliance voltage such that it is always at an optimal level in order to effectively and efficiently deliver stimulation current to one or more stimulation sites within a patient. The systems and methods facilitate such dynamic compliance voltage by dynamically adjusting a transmit power level supplied to implantable stimulator 104.

Figure 6:
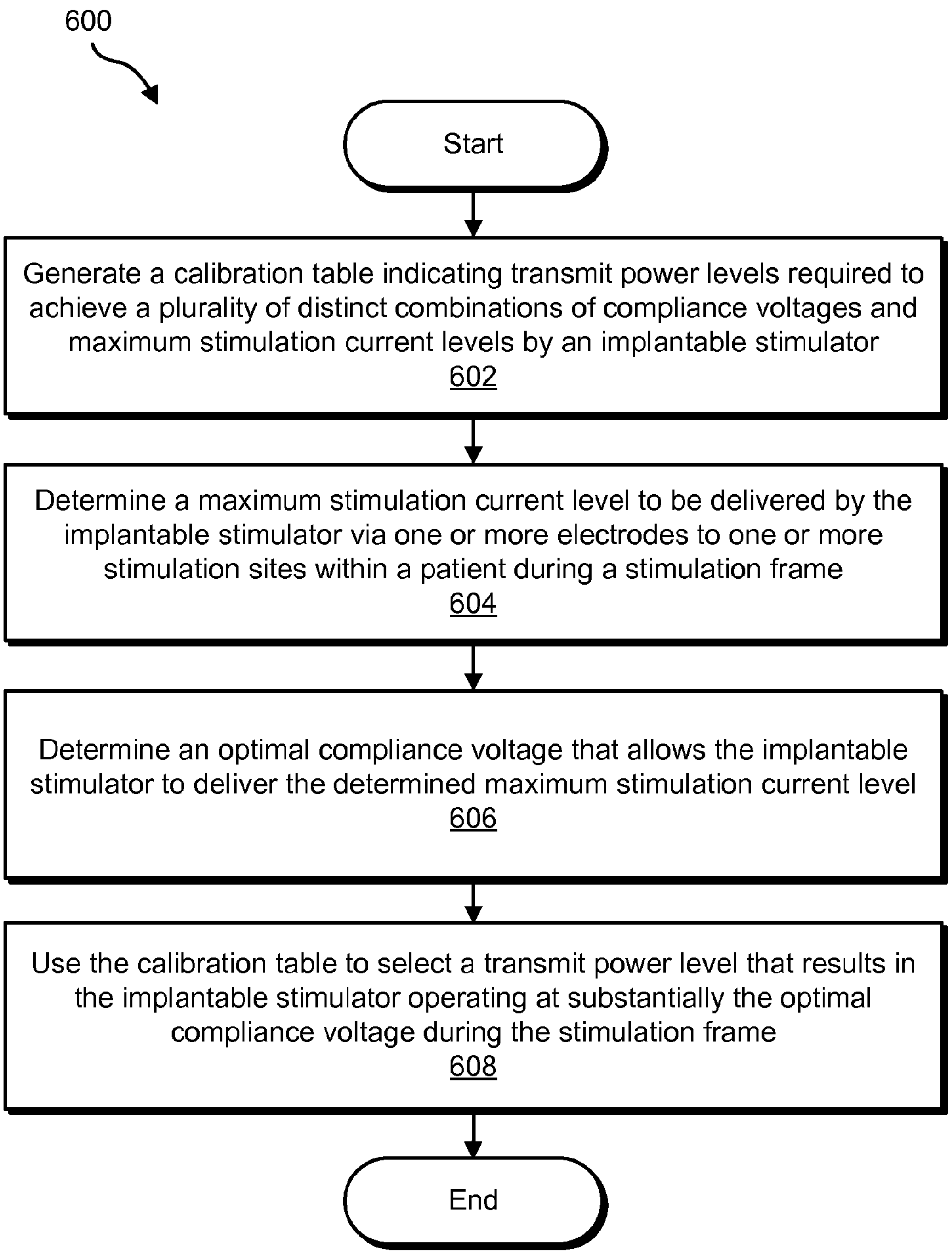
FIG. 6 illustrates an exemplary method of dynamically managing a compliance voltage of an implantable stimulator according to principles described herein.

For example, FIG. 6 illustrates an exemplary method 600 of dynamically managing a compliance voltage of an implantable stimulator (e.g., implantable stimulator 104). Method 600 may be used by an external control device (e.g., external control device 102) to maintain the compliance voltage within the implantable stimulator at an optimal level in order to effectively and efficiently deliver stimulation current to one or more stimulation sites within a patient. While FIG. 6 illustrates exemplary steps according to one embodiment, other embodiments may omit, add to, reorder, and/or modify any of the steps shown in FIG. 6.

In step 602, a calibration table indicating transmit power levels required to achieve a plurality of distinct combinations of compliance voltages and maximum stimulation current levels by an implantable stimulator is generated. The calibration table may be generated in any suitable manner as may serve a particular application.

For example, calibration facility 204 may fix the compliance voltage within implantable stimulator 104 at a particular level and vary the transmit power level of the power signal transmitted by communication facility 202 to implantable stimulator 104. At each distinct transmit power level, calibration facility 204 may measure a maximum stimulation current level achievable by a current source included within implantable stimulator 104 while still maintaining the fixed compliance voltage. If implantable stimulator 104 is multi-channel (i.e., includes multiple current sources each corresponding to one of a plurality of electrodes), the maximum stimulation current achievable by each current source at the fixed compliance voltage and at the different transmit power levels may be measured and averaged for inclusion in the calibration table. Calibration facility 204 may then fix the compliance voltage at a new level and repeat the measurements of maximum stimulation current levels achievable by each of the current sources at each of the distinct transmit power levels.

FIG. 7 illustrates an exemplary calibration table 700 that may be generated by calibration facility 204. As shown in FIG. 7, calibration table 700 lists various transmit power levels required to achieve various combinations of fixed target voltages and maximum stimulation current levels by implantable stimulator 104. For example, the first row (i.e., row 702) of calibration table 700 indicates that in order to achieve a maximum stimulation current level of 1000 microamps and a compliance voltage of 8 volts, a 70 milliwatt (mW) transmit power level is required. However, as shown in the second row (i.e., row 704) of calibration table 700, a transmit power of only 75 mW is required to achieve a maximum stimulation current level of 1000 microamps and a compliance voltage of 7 volts. Transmit power level requirements for other combinations of compliance voltages and maximum stimulation current levels may be included in calibration table 700, as shown in FIG. 7.

The number of entries included within calibration table 700 may vary as may serve a particular application. For example, calibration facility 204 may be configured to step through different compliance voltages in one volt increments, as shown in calibration table 700. Finer resolutions (e.g., half volt increments) may be used in order to realize more accurate compliance voltage management. Likewise, the step size in maximum stimulation current levels included within calibration table 700 may be varied as may serve a particular application.

In some examples, calibration facility 204 may be configured to direct implantable stimulator 104 to shunt a current path of each of the current sources through a shunt resistor while the measurements used to generate the calibration table are performed. This may be beneficial in the context of a cochlear implant system (e.g., cochlear implant system 500), for example, in order to minimize patient perception of the stimulation current that is applied to the various electrodes during the calibration procedure.

Figure 8:
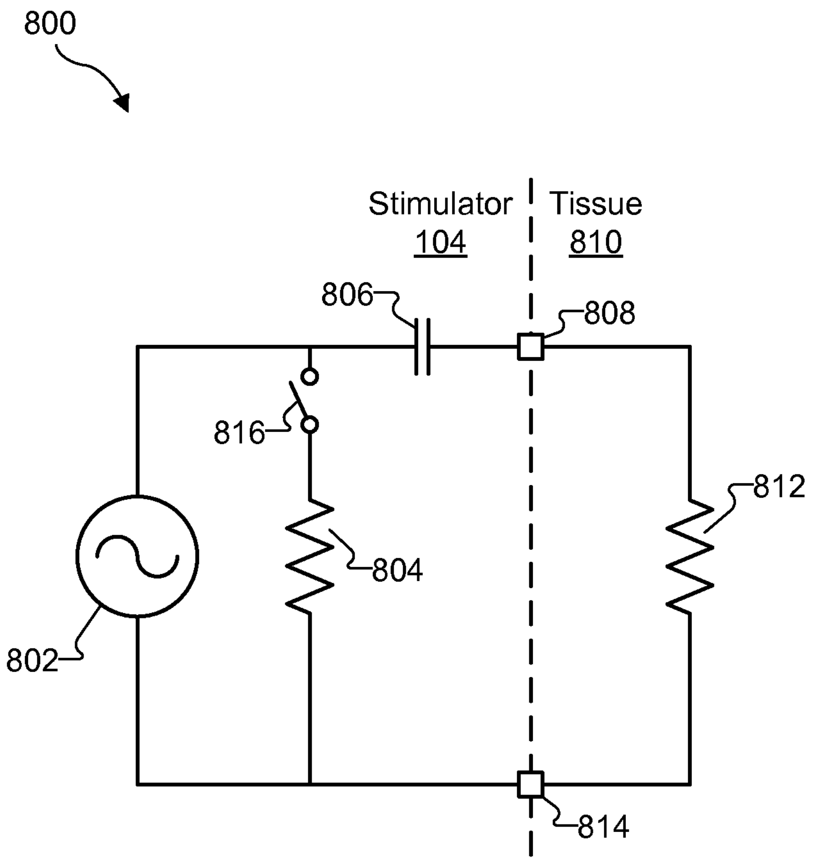
FIG. 8 illustrates exemplary shunt circuitry according to principles described herein.

FIG. 8 illustrates exemplary shunt circuitry 800 that may be included within implantable stimulator 104 and that may be used to shunt a current path of each current source (e.g., current source 802) through a shunt resistor 804. In some examples, the same shunt circuitry 800 is used for each current source in a multi-channel implantable stimulator. Alternatively, replicas of shunt circuitry 800 may be included in implantable stimulator 104 for each of the current sources.

As shown in FIG. 8, stimulation current generated by current source 804 typically passes through a DC blocking capacitor 806, through a stimulating electrode 808 that corresponds to current source 802, and into tissue 810. Tissue 810 may include tissue located at a stimulation site associated with stimulating electrode 808. The impedance of tissue 810 and of stimulating electrode 808 itself is referred to as an electrode impedance associated with stimulating electrode 808 and may be represented by resistor 812. The stimulation current may exit tissue 810 by way of a return electrode 814. Return electrode 814 may include another electrode disposed on a lead (e.g., lead 512), a case or housing of implantable stimulator 104, and/or any other conductive component configured to serve as a return for the stimulation current.

Prior to performing a calibration procedure that generates a calibration table, calibration facility 204 may direct implantable stimulator 104 to close switch 816, thereby placing shunt resistor 804 in parallel with stimulating electrode 808. In this manner, the current path of current source 802 may be shunted through shunt resistor 804 during the calibration procedure such that patient perception of the stimulation current generated by current source 802 is minimized. Shunt resistor 804 may have any suitable resistance as may serve a particular application.

An example will now be given of a calibration procedure that utilizes shunt circuitry 800. Calibration facility 204 may first direct implantable stimulator 104 to close switch 816 in order to shunt a current path of current source 802 through shunt resistor 804. Calibration facility 204 may then select a target compliance voltage (e.g., 8 volts) and adjust a transmit power level of the power signal supplied by communication facility 202 in order to achieve the selected compliance voltage.

Calibration facility 204 may then direct current source 802 to output a stimulation current and increase an amplitude thereof until a maximum stimulation current level sustainable at the transmit power level and target compliance voltage is achieved. To illustrate, calibration facility 204 may direct current source 802 to increase a stimulation current level of the stimulation current output by current source 802 until a maximum stimulation current level (e.g., 1000 microamps) sustainable at a compliance voltage of 8 volts and a transmit power level of 70 mW is achieved.

Calibration facility 204 may be configured to determine whether a particular stimulation current level is sustainable at a particular target compliance voltage in any suitable manner as may serve a particular application. For example, the stimulation current may be increased until clipping of the stimulation current occurs and/or until any other event occurs that is indicative of a maximum sustainable stimulation current at the target compliance voltage.

Calibration facility 204 may then sequentially decrease the transmit power level to one or more new transmit power levels (e.g., 60 mW, 50 mW, etc.) while maintaining the fixed compliance voltage and measure maximum stimulation current levels achievable at each of the new transmit power levels. This process may be repeated for each current source included within implantable stimulator 104. The resulting transmit power levels across each of the current sources and for each respective combination of compliance voltage and maximum stimulation current level may be averaged and recorded to calibration table 700.

The overall process of determining maximum stimulation current levels sustainable at different combinations of transmit power level and target compliance voltage may be repeated for each of a number of different fixed compliance voltages (e.g., 7 volts, 6 volts, 5 volts, etc.). The resulting data may be recorded to calibration table 700. The number of fixed compliance voltages used to generate stimulation table 700 may vary depending on the desired resolution and accuracy of a particular system 100.

In some examples, the calibration table may be generated during a calibration procedure performed during a start up routine of external control device 102. The calibration table may be alternatively generated at any other time (e.g., during a fitting session, on a periodic basis, etc.) and/or in response to any event as may serve a particular application. In this manner, equipment changes (e.g., switching out of a sound processor or other external control device for a new one), physiological changes (changes in flap thickness, hair growth, etc.), positioning changes (e.g., a change in the separation distance between the communication coils of external control device 102 and implantable stimulator 104), and/or any other factor that may affect the relationship between the values included within the calibration table may be accounted for on a periodic basis and/or as needed.

Returning to FIG. 6, in step 604, a maximum stimulation current level to be delivered by the implantable stimulator via one or more electrodes to one or more stimulation sites within a patient during a stimulation frame is determined. For example, external control device 102 may analyze stimulation parameter data to determine the maximum stimulation current level to be delivered by implantable stimulator 104 during a given stimulation frame. To illustrate, sound processor 504 may identify spectral content included within a frequency domain representation of an audio signal presented to a patient that includes a maximum amount of energy compared to other spectral content to be presented to the user during a particular stimulation frame. Sound processor 504 may then analyze mapping data to determine a stimulation current level that corresponds to the maximum amount of energy and designate the determined stimulation current level as the maximum stimulation current level to be applied to the patient during the stimulation frame.

External control device 102 may further identify the particular electrode that is to apply the maximum stimulation current. In this manner, as will be described in more detail below, the impedance of that electrode may be used along with the determined maximum stimulation current level to determine an optimal compliance voltage in step 606.

In step 606, an optimal compliance voltage that allows the implantable stimulator to deliver the maximum stimulation current level is determined. For example, compliance voltage management facility 206 may compute the optimal compliance voltage by multiplying an impedance of the electrode that is to deliver the maximum stimulation current level by the maximum stimulation current level determined in step 604. In some examples, a headroom voltage may be optionally included in the computed optimal compliance voltage in order to ensure that the computed optimal compliance voltage is large enough for the implantable stimulator to actually deliver the maximum stimulation current level.

To this end, compliance voltage management facility 206 may be configured to measure and record impedances of each of the electrodes electrically coupled to implantable stimulator 104. The electrode impedances may be measured in any suitable manner as may serve a particular application. For example, compliance voltage management facility 206 may direct implantable stimulator 104 to apply a known stimulation current to each of the electrodes and then measure the resulting voltages at each electrode. The impedance of each electrode may then be determined by dividing the measured voltages by the known stimulation current. It will be recognized that any other method of detecting electrode impedances may be performed by compliance voltage management facility 206 as may serve a particular application.

Compliance voltage facility 206 may measure and record electrode impedances at any time as may serve a particular application. For example, compliance voltage facility 206 may measure and record electrode impedances during a calibration procedure performed during a start up routine of external control device 102, during a fitting session, on a periodic basis, and/or in response to any event as may serve a particular application. Repeated measurements of the electrode impedances may detect any change in the electrode impedances that may occur over time. In some examples, compliance voltage facility 206 may measure and record each of the electrode impedances prior to performing step 606 so that the measurements of the electrode impedances do not have to be performed in real-time as step 606 is performed.

Once the optimal compliance voltage has been determined in step 606, the calibration table may be used to select a transmit power level that results in the implantable stimulator operating at substantially the optimal compliance voltage during a stimulation frame, as shown in step 608. For example, compliance voltage management facility 206 may refer to the calibration table to identify a combination of maximum stimulation current level and compliance voltage listed therein that most closely matches the maximum stimulation current level and the optimal compliance voltage determined in steps 604 and 606, respectively. Compliance voltage management facility 206 may then select the transmit power level listed in the calibration table that corresponds to the identified combination and direct communication facility 202 to transmit a power signal having the selected transmit power level to implantable stimulator 104 during the stimulation frame.

In some alternative examples, compliance voltage management facility 206 may adjust the transmit power level at some point not necessarily related to a stimulation frame. For example, the transmit power level may be adjusted at any point to account for one or more dynamics of the tank circuit, a rate of fluctuation in speech energy, and/or any other factor as may serve a particular application.

It will be recognized that method 600 may be performed during different phases. For example, step 602 may be performed during a calibration phase and steps 604-608 may be performed in real-time during a stimulation phase that follows the calibration phase.

In some examples, the dynamics of the tank circuit (e.g., tank circuit 400) that generates the compliance voltage may be accounted for in accordance with the methods and systems described herein. For example, it may not be possible to adjust the compliance voltage instantaneously or to make a relatively large adjustment in the compliance voltage. To illustrate, it may take several milliseconds to adjust the compliance voltage from one value to another. Hence, in some examples, external control device 102 may be configured to direct implantable stimulator 104 to begin transitioning from one voltage to another during a time period that is sufficiently in advance of the stimulation frame in which the new compliance voltage level is to be maintained.

Figure 9:
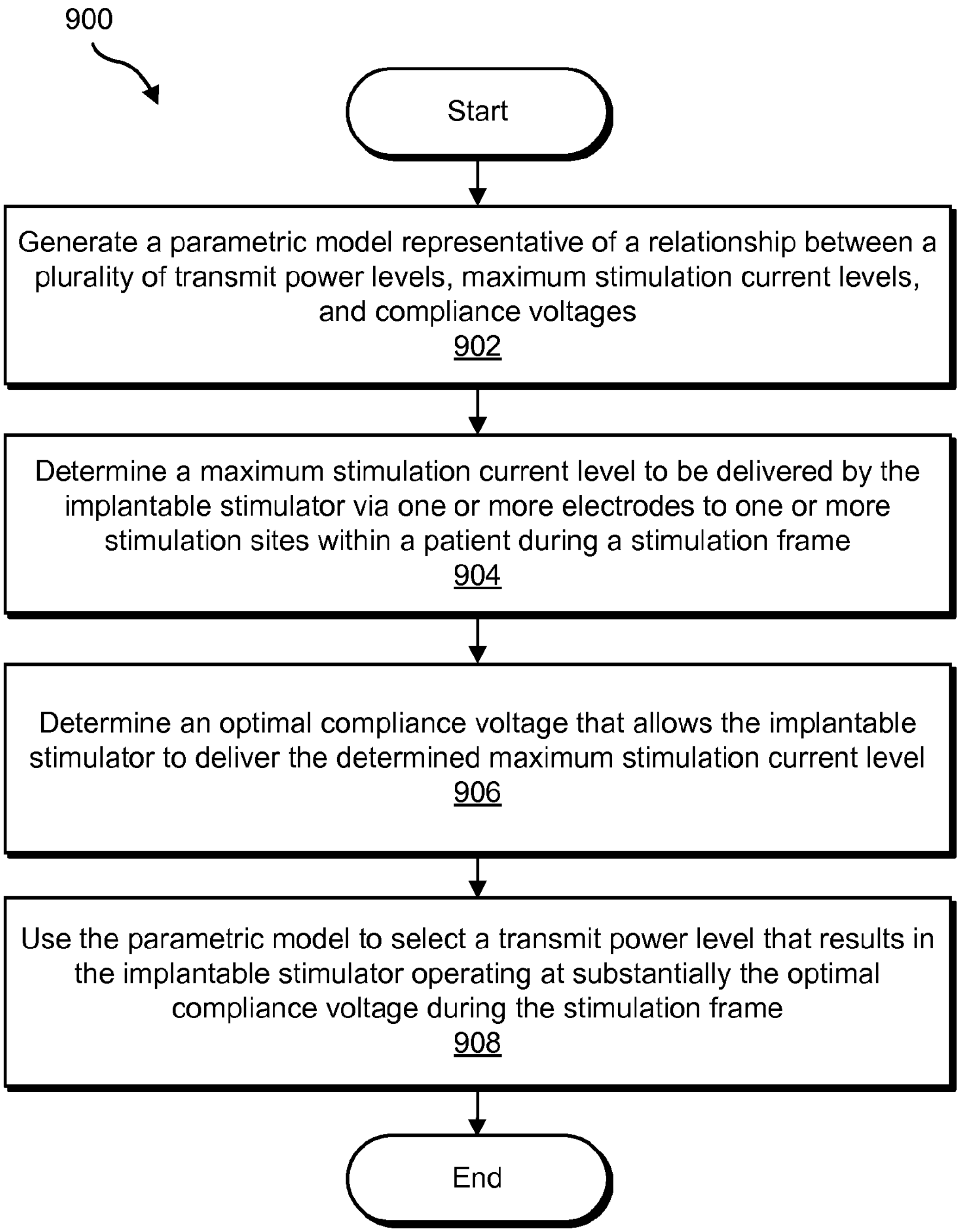
FIG. 9 illustrates another exemplary method of dynamically managing a compliance voltage of an implantable stimulator according to principles described herein.

FIG. 9 illustrates another exemplary method 900 of dynamically managing a compliance voltage of an implantable stimulator (e.g., implantable stimulator 104). While FIG. 9 illustrates exemplary steps according to one embodiment, other embodiments may omit, add to, reorder, and/or modify any of the steps shown in FIG. 9.

In step 902, a parametric model representative of a relationship between a plurality of transmit power levels, maximum stimulation current levels, and compliance voltages is generated. The parametric model may be generated by calibration facility 204 in any suitable manner. To illustrate, Equation 1 shows an exemplary parametric model that may be generated by calibration facility 204:

$$I_{max} = f(RF, V_{comp}) = \frac{RF^2 * V_{comp}}{k} \quad \text{(Equation 1)}$$

In Equation 1, $I_{max}$ represents maximum stimulation current level, RF represents transmit power level, $V_{comp}$ represents compliance voltage, and k represents a fixed physiological parameter. Hence, Equation 1 shows that a maximum stimulation current level may be represented as a function of a particular transmit power level and a particular compliance voltage.

In some examples, the physiological parameter may be generated by calibration facility 204 during a calibration procedure. Once the physiological parameter has been determined, the parametric model represented by Equation 1 may be used to determine a transmit power level that results in implantable stimulator 104 operating an optimal compliance voltage during a particular stimulation frame.

Figure 10:
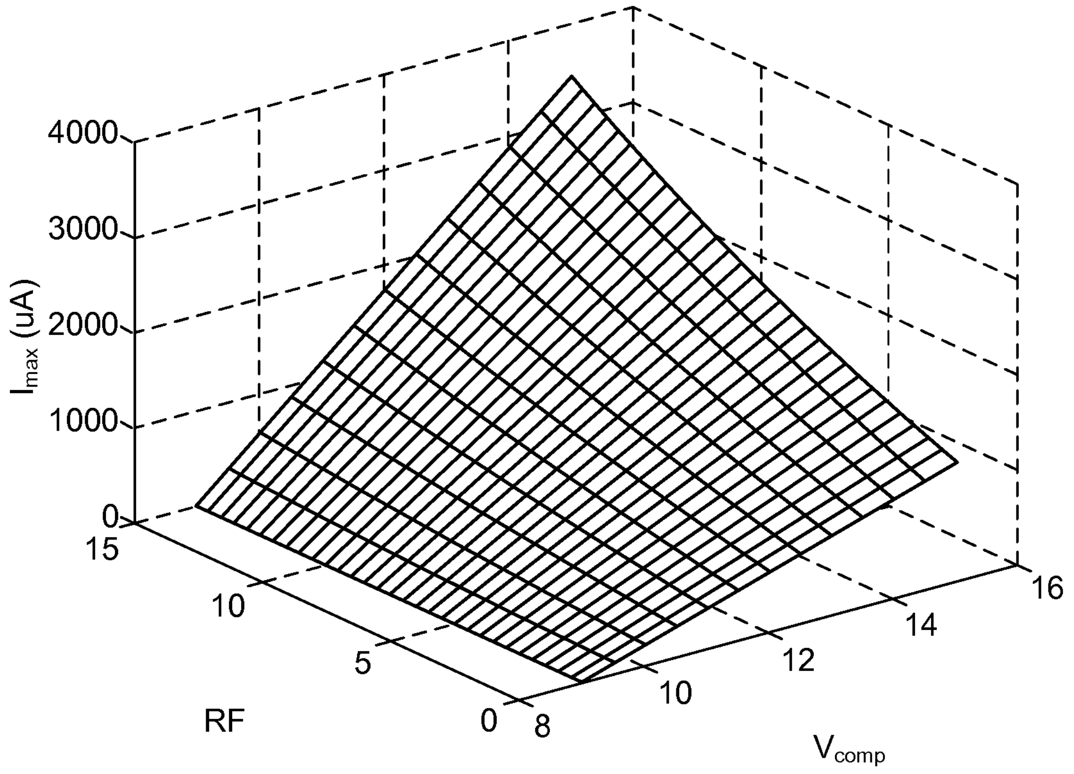
FIG. 10 illustrates an exemplary plot of a parametric model according to principles described herein.

To illustrate, FIG. 10 illustrates an exemplary plot 1000 of a parametric model represented by Equation 1, where the physiological parameter k is equal to 0.92. Plot 1000 illustrates that the parametric model may be used to select a transmit power level that results in a desired combination of maximum stimulation current level and compliance voltage.

Calibration facility 204 may determine the physiological parameter k in any suitable manner. For example, calibration facility 204 may measure the transmit power level required to sustain a discreet number of maximum stimulation current levels at a particular compliance voltage level. Calibration facility 204 may then fit a curve represented by Equation 2 below to the measured transmit power levels to determine an optimal value for the physiological parameter k.

$$RF_{req} = k + e^{I_{max}/1024} \quad \text{(Equation 2)}$$

Equation 2 is illustrative of the many different equations that may be fitted to the measured transmit power levels in order to determine an optimal value for the physiological parameter k. In Equation 2, $RF_{req}$ represents a transmit power level required to sustain a maximum current level ($I_{max}$) at a particular compliance voltage level. Calibration facility 204 may fit Equation 2 to the measured transmit power levels to determine an optimum value for the physiological parameter k.

Figure 11:
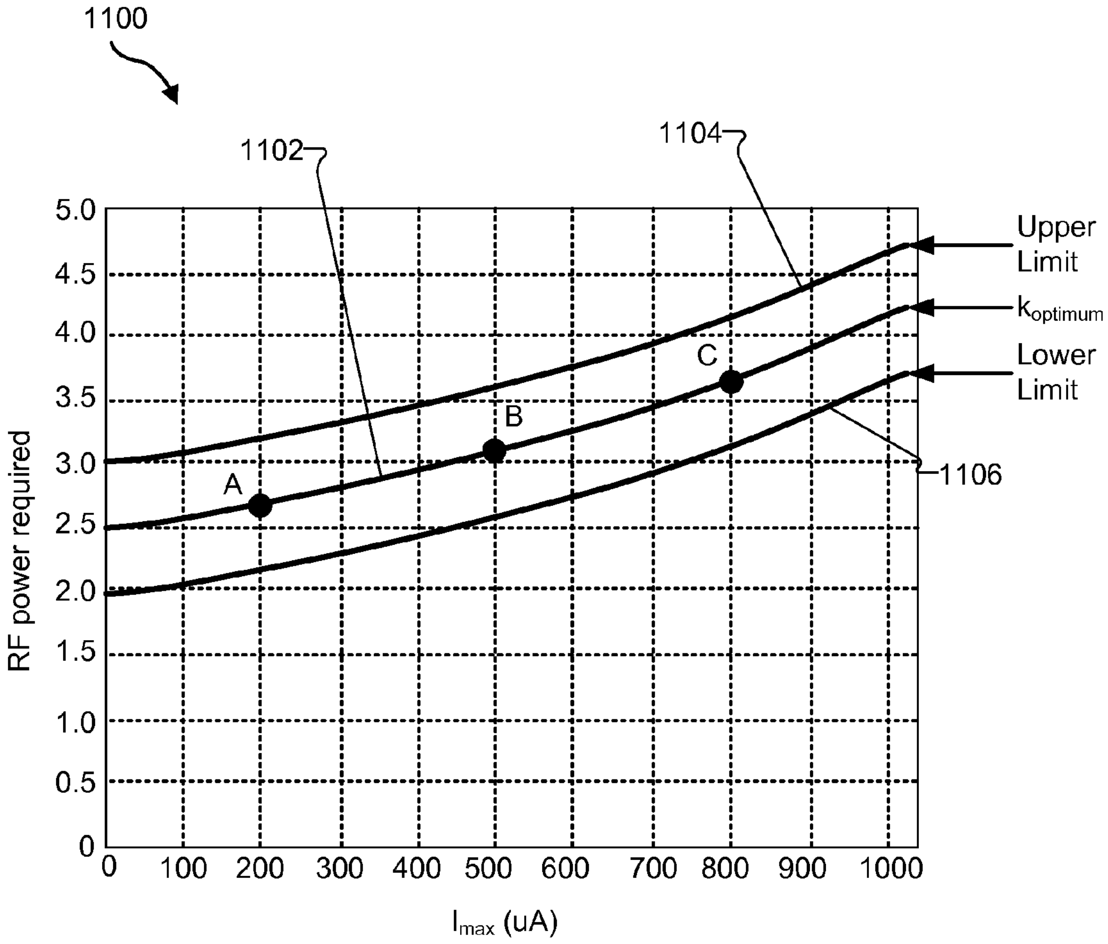
FIG. 11 illustrates a graph illustrative of a method of determining an optimal physiological parameter according to principles described herein.

To illustrate, calibration facility 204 may measure the transmit power level required to sustain maximum stimulation current levels of 200, 500, and 800 microamps at a particular compliance voltage level. FIG. 11 illustrates a graph 1100 with the measured transmit power levels plotted thereon (points A, B, and C, respectively). Calibration facility 204 may fit a curve represented by Equation 2 to the measured transmit power levels (i.e., points A, B, and C). To this end, a value for the physiological parameter k may be selected that results in the curve represented by Equation 2 most closely passing through points A, B, and C. For example, curve 1102 shown in FIG. 11 represents Equation 2 after an optimal value for the physiological parameter k has been selected to fit curve 1102 to points A, B, and C. In some examples, upper and lower limits (represented by curves 1104 and 1106, respectively) may be provided within which calibration facility 204 may limit its search for an optimal value for the physiological parameter k.

In some examples, the parametric model may be determined during a calibration procedure performed during a start up routine of external control device 102. The parametric model may be alternatively determined and/or updated at any other time (e.g., during a fitting session, on a periodic basis, etc.) and/or in response to any event as may serve a particular application. In this manner, equipment changes (e.g., switching out of a sound processor or other external control device for a new one), physiological changes (changes in flap thickness, hair growth, etc.), positioning changes (e.g., a change in the separation distance between the communication coils of external control device 102 and implantable stimulator 104), and/or any other factor that may affect the relationship between the values included within the parametric model may be accounted for on a periodic basis and/or as needed.

Returning to FIG. 9, in step 904, a maximum stimulation current level to be delivered by the implantable stimulator via one or more electrodes to one or more stimulation sites within a patient during a stimulation frame is determined. This determination may be performed in any of the ways described herein.

In step 906, an optimal compliance voltage that allows the implantable stimulator to deliver the maximum stimulation current level determined in step 904 is determined. This determination may be performed in any of the ways described herein.

Once the optimal compliance voltage has been determined in step 906, the parametric model generated in step 902 may be used to select a transmit power level that results in the implantable stimulator operating at substantially the optimal compliance voltage during a stimulation frame, as shown in step 608. For example, compliance voltage management facility 206 may refer to the parametric model to identify a transmit power level that results in a desired combination of maximum stimulation current level and compliance voltage. Compliance voltage management facility 206 may then select the identified transmit power level and direct communication facility 202 to transmit a power signal having the identified transmit power level to implantable stimulator 104 during the stimulation frame.

In some examples, it may be advantageous to use a parametric model because relatively few measurements have to be made by calibration facility 204 during a calibration procedure. For example, as illustrated above, calibration facility 204 may only be required to measure transmit power levels required to sustain three discreet maximum stimulation current levels. It will be recognized that three measurements is merely illustrative and that calibration facility 204 may alternatively make any other number of measurements as may serve a particular implementation.

In some examples, the parametric model may be used to generate a calibration table having any suitable resolution (e.g., a resolution of 50 microamps). The calibration table may then be used to select a transmit power that results in implantable stimulator 104 operating at an optimal compliance voltage during a particular stimulation frame. Additionally or alternatively, the parametric model may be used to interpolate between multiple calibration tables.

As mentioned, the methods, apparatuses, and systems described herein facilitate dynamic compliance voltage management for an implantable stimulator. For example, an exemplary method includes generating, by an external control device selectively and communicatively coupled to an implantable stimulator, a calibration table indicating transmit power levels required to achieve a plurality of distinct combinations of compliance voltages and maximum stimulation current levels by the implantable stimulator; determining, by the external control device, a maximum stimulation current level to be delivered by the implantable stimulator via one or more electrodes to one or more stimulation sites within a patient during a stimulation frame; determining, by the external control device, an optimal compliance voltage that allows the implantable stimulator to deliver the determined maximum stimulation current level; and selecting, by the external control device in accordance with the calibration table, a transmit power level that results in the implantable stimulator operating at substantially the optimal compliance voltage during the stimulation frame.

Another exemplary method includes generating, by an external control device selectively and communicatively coupled to an implantable stimulator, a parametric model representative of a relationship between a plurality of transmit power levels, a plurality of maximum stimulation current levels, and a plurality of compliance voltages; determining, by the external control device, a maximum stimulation current level to be delivered by the implantable stimulator via one or more electrodes to one or more stimulation sites within a patient during a stimulation frame; determining, by the external control device, an optimal compliance voltage that allows the implantable stimulator to deliver the determined maximum stimulation current level; and selecting, by the external control device in accordance with the parametric model, a transmit power level that results in the implantable stimulator operating at substantially the optimal compliance voltage during the stimulation frame.

An exemplary apparatus includes (1) a communication facility configured to transmit a power signal to an implantable stimulator, (2) a calibration facility configured to generate a calibration table indicating transmit power levels required to achieve a plurality of distinct combinations of compliance voltages and maximum stimulation current levels by the implantable stimulator, and (3) a compliance voltage facility. The compliance voltage facility is configured to (a) determine a maximum stimulation current level to be delivered by the implantable stimulator via one or more electrodes to one or more stimulation sites within a patient during a stimulation frame, (b) determine an optimal compliance voltage that allows the implantable stimulator to deliver the determined maximum stimulation current level, and (c) select, in accordance with the calibration table, a transmit power level that results in the implantable stimulator operating at substantially the optimal compliance voltage during the stimulation frame.

Another exemplary apparatus includes (1) a communication facility configured to transmit a power signal to an implantable stimulator (where the implantable stimulator is configured to derive a compliance voltage from the power signal); (2) a calibration facility configured to generate a parametric model representative of a relationship between a plurality of transmit power levels, a plurality of maximum stimulation current levels, and a plurality of compliance voltages; and (3) a compliance voltage facility configured to (a) determine a maximum stimulation current level to be delivered by the implantable stimulator via one or more electrodes to one or more stimulation sites within a patient during a stimulation frame, (b) determine an optimal compliance voltage that allows the implantable stimulator to deliver the determined maximum stimulation current level, and (c) select, in accordance with the parametric model, a transmit power level that results in the implantable stimulator operating at substantially the optimal compliance voltage during the stimulation frame.

An exemplary cochlear implant system includes (1) an implantable cochlear stimulator configured to generate and apply stimulation current to one or more stimulation sites within a cochlea of a patient via one or more electrodes and (2) a sound processor selectively and communicatively coupled to the implantable cochlear stimulator. The sound processor is configured to (a) transmit a power signal to the implantable cochlear stimulator; (b) generate a calibration table indicating transmit power levels required to achieve a plurality of distinct combinations of compliance voltages and maximum stimulation current levels by the implantable cochlear stimulator; (c) determine a maximum stimulation current level to be delivered by the implantable cochlear stimulator during a stimulation frame; (d) determine an optimal compliance voltage that allows the implantable cochlear stimulator to deliver the determined maximum stimulation current level; and (e) select, in accordance with the calibration table, a transmit power level that results in the implantable cochlear stimulator operating at substantially the optimal compliance voltage during the stimulation frame.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:

generating, by an external control device selectively and communicatively coupled to an implantable stimulator, a calibration table indicating transmit power levels required to be transmitted from the external control device to the implantable stimulator to achieve a plurality of distinct combinations of compliance voltages and maximum stimulation current levels by the implantable stimulator;

determining, by the external control device, a maximum stimulation current level to be delivered by the implantable stimulator via one or more electrodes to one or more stimulation sites within a patient during a stimulation frame;

determining, by the external control device, an optimal compliance voltage that allows the implantable stimulator to deliver the determined maximum stimulation current level; and selecting, by the external control device in accordance with the calibration table, a transmit power level that results in the implantable stimulator operating at the optimal compliance voltage during the stimulation frame;

wherein the implantable stimulator comprises a plurality of current sources and wherein the generating of the calibration table comprises:

directing the implantable stimulator to sequentially shunt a current path of each of the current sources through a shunt resistor; and recording, for each of a plurality of distinct number of fixed compliance voltages, a transmit power level required to maximize a stimulation current generated by each of the current sources while shunted.

2. The method of claim 1, further comprising:

transmitting, by the external control device, a power signal having the selected transmit power level to the implantable stimulator during the stimulation frame, wherein the implantable stimulator is configured to derive an operating voltage having the operating voltage level from the power signal.

3. The method of claim 1, further comprising recording, by the external control device, an impedance of each of the one or more electrodes.

4. The method of claim 1, further comprising performing the generating of the calibration table during a calibration phase of the implantable stimulator.

5. The method of claim 1, wherein the stimulation frame comprises a time period during which a predetermined number of stimulation pulses are delivered to the one or more stimulation sites via the one or more electrodes.

6. The method of claim 1, further comprising:

determining, by the external control device, another maximum stimulation current level to be delivered by the implantable stimulator via the one or more electrodes to the one or more stimulation sites during another stimulation frame;

determining, by the external control device, another optimal compliance voltage that allows the implantable stimulator to deliver the determined another maximum stimulation current level during the another stimulation frame; and selecting, by the external control device in accordance with the calibration table, another transmit power level that results in the implantable stimulator operating at the another optimal compliance voltage during the another stimulation frame.

7. A method comprising:

generating, by an external control device selectively and communicatively coupled to an implantable stimulator, a calibration table indicating transmit power levels required to be transmitted from the external control device to the implantable stimulator to achieve a plurality of distinct combinations of compliance voltages and maximum stimulation current levels by the implantable stimulator;

determining, by the external control device, a maximum stimulation current level to be delivered by the implantable stimulator via one or more electrodes to one or more stimulation sites within a patient during a stimulation frame;

recording, by the external control device, an impedance of each of the one or more electrodes;

determining, by the external control device, an optimal compliance voltage that allows the implantable stimulator to deliver the determined maximum stimulation current level; and selecting, by the external control device in accordance with the calibration table, a transmit power level that results in the implantable stimulator operating at the optimal compliance voltage during the stimulation frame;

wherein the determining of the optimal compliance voltage comprises multiplying the determined maximum stimulation current level by the recorded impedance of an electrode included within the one or more electrodes through which the stimulation current having the maximum stimulation current level is to be delivered.

8. The method of claim 7, further comprising performing the recording of the impedance of each of the one or more electrodes during a calibration phase of the implantable stimulator.

9. The method of claim 7, further comprising periodically performing the recording of the impedance of each of the one or more electrodes.

10. The method of claim 7, further comprising transmitting, by the external control device, a power signal having the selected transmit power level to the implantable stimulator during the stimulation frame, wherein the implantable stimulator is configured to derive an operating voltage having the operating voltage level from the power signal.

11. The method of claim 7, further comprising:

determining, by the external control device, another maximum stimulation current level to be delivered by the implantable stimulator via the one or more electrodes to the one or more stimulation sites during another stimulation frame;

determining, by the external control device, another optimal compliance voltage that allows the implantable stimulator to deliver the determined another maximum stimulation current level during the another stimulation frame; and selecting, by the external control device in accordance with the calibration table, another transmit power level that results in the implantable stimulator operating at the another optimal compliance voltage during the another stimulation frame.

12. A method comprising:

generating, by an external control device selectively and communicatively coupled to an implantable stimulator, a calibration table indicating transmit power levels required to be transmitted from the external control device to the implantable stimulator to achieve a plurality of distinct combinations of compliance voltages and maximum stimulation current levels by the implantable stimulator;

determining, by the external control device, a maximum stimulation current level to be delivered by the implantable stimulator via one or more electrodes to one or more stimulation sites within a patient during a stimulation frame;

determining, by the external control device, an optimal compliance voltage that allows the implantable stimulator to deliver the determined maximum stimulation current level;

selecting, by the external control device in accordance with the calibration table, a transmit power level that results in the implantable stimulator operating at the optimal compliance voltage during the stimulation frame; and periodically performing the generating of the calibration table.

13. The method of claim 12, further comprising transmitting, by the external control device, a power signal having the selected transmit power level to the implantable stimulator during the stimulation frame, wherein the implantable stimulator is configured to derive an operating voltage having the operating voltage level from the power signal.

14. The method of claim 12, further comprising:

determining, by the external control device, another maximum stimulation current level to be delivered by the implantable stimulator via the one or more electrodes to the one or more stimulation sites during another stimulation frame;

determining, by the external control device, another optimal compliance voltage that allows the implantable stimulator to deliver the determined another maximum stimulation current level during the another stimulation frame; and selecting, by the external control device in accordance with the calibration table, another transmit power level that results in the implantable stimulator operating at the another optimal compliance voltage during the another stimulation frame.

15. A method comprising:

generating, by an external control device selectively and communicatively coupled to an implantable stimulator each time the external control device is powered on or coupled to the implantable stimulator, a calibration table indicating transmit power levels required to be transmitted from the external control device to the implantable stimulator to achieve a plurality of distinct combinations of compliance voltages and maximum stimulation current levels by the implantable stimulator;

determining, by the external control device, a maximum stimulation current level to be delivered by the implantable stimulator via one or more electrodes to one or more stimulation sites within a patient during a stimulation frame;

determining, by the external control device, an optimal compliance voltage that allows the implantable stimulator to deliver the determined maximum stimulation current level; and selecting, by the external control device in accordance with the calibration table, a transmit power level that results in the implantable stimulator operating at the optimal compliance voltage during the stimulation frame.

16. The method of claim 15, further comprising transmitting, by the external control device, a power signal having the selected transmit power level to the implantable stimulator during the stimulation frame, wherein the implantable stimulator is configured to derive an operating voltage having the operating voltage level from the power signal.

17. The method of claim 15, further comprising:

determining, by the external control device, another maximum stimulation current level to be delivered by the implantable stimulator via the one or more electrodes to the one or more stimulation sites during another stimulation frame;

determining, by the external control device, another optimal compliance voltage that allows the implantable stimulator to deliver the determined another maximum stimulation current level during the another stimulation frame; and selecting, by the external control device in accordance with the calibration table, another transmit power level that results in the implantable stimulator operating at the another optimal compliance voltage during the another stimulation frame.

18. An apparatus comprising:

a communication facility configured to transmit a power signal from an external control device to an implantable stimulator, the implantable stimulator being configured to derive a compliance voltage from the power signal;

a calibration facility configured to generate a calibration table indicating transmit power levels required to be transmitted from the external control device to the implantable stimulator to achieve a plurality of distinct combinations of compliance voltages and maximum stimulation current levels by the implantable stimulator; and a compliance voltage facility configured to determine a maximum stimulation current level to be delivered by the implantable stimulator via one or more electrodes to one or more stimulation sites within a patient during a stimulation frame, determine an optimal compliance voltage that allows the implantable stimulator to deliver the determined maximum stimulation current level, and select, in accordance with the calibration table, a transmit power level that results in the implantable stimulator operating at the optimal compliance voltage during the stimulation frame wherein the implantable stimulator comprises a plurality of current sources and wherein the calibration facility is configured to generate the calibration table by:

directing the implantable stimulator to sequentially shunt a current path of each of the current sources through a shunt resistor; and recording, for each of a plurality of distinct number of fixed compliance voltages, a transmit power level required to maximize a stimulation current generated by each of the current sources while shunted.

19. The apparatus of claim 18, wherein the compliance voltage facility is further configured to direct the communication facility to transmit a power signal having the selected transmit power level to the implantable stimulator during the stimulation frame.

20. The apparatus of claim 18, wherein the compliance voltage facility is further configured to record an impedance of each of the one or more electrodes.

21. The apparatus of claim 18, wherein the compliance voltage facility is further configured to:

determine another maximum stimulation current level to be delivered by the implantable stimulator via the one or more electrodes to the one or more stimulation sites during another stimulation frame;

determine another optimal compliance voltage that allows the implantable stimulator to deliver the determined another maximum stimulation current level during the another stimulation frame; and select, in accordance with the calibration table, another transmit power level that results in the implantable stimulator operating at the another optimal compliance voltage during the another stimulation frame.

22. An apparatus comprising:

a communication facility configured to transmit a power signal from an external control device to an implantable stimulator, the implantable stimulator being configured to derive a compliance voltage from the power signal;

a calibration facility configured to generate a calibration table indicating transmit power levels required to be transmitted from the external control device to the implantable stimulator to achieve a plurality of distinct combinations of compliance voltages and maximum stimulation current levels by the implantable stimulator; and a compliance voltage facility configured to determine a maximum stimulation current level to be delivered by the implantable stimulator via one or more electrodes to one or more stimulation sites within a patient during a stimulation frame, record an impedance of each of the one or more electrodes, determine an optimal compliance voltage that allows the implantable stimulator to deliver the determined maximum stimulation current level, and select, in accordance with the calibration table, a transmit power level that results in the implantable stimulator operating at the optimal compliance voltage during the stimulation frame;

wherein the compliance voltage facility is further configured to determine the optimal compliance voltage by multiplying the determined maximum stimulation current level by the recorded impedance of an electrode included within the one or more electrodes through which the stimulation current having the maximum stimulation current level is to be delivered.

23. The apparatus of claim 22, wherein the compliance voltage facility is further configured to direct the communication facility to transmit a power signal having the selected transmit power level to the implantable stimulator during the stimulation frame.

* * * * *